(12) United States Patent
Lambris et al.

(10) Patent No.: US 6,699,481 B2
(45) Date of Patent: Mar. 2, 2004

(54) PEPTIDES FOR INHIBITION OF HERPES SIMPLEX VIRUS ENTRY

(75) Inventors: John D. Lambris, Bryn Mawr, PA (US); Maria Rosa Sarrias, Philadelphia, PA (US); Gary H. Cohen, Havertown, PA (US); Roselyn J. Eisenberg, Haddonfield, NJ (US); Patricia G. Spear, Chicago, IL (US); Rebecca I. Montgomery, Lodi, WI (US)

(73) Assignees: The Trustees of the University of Pennsylvania, Philadelphia, PA (US); Northwestern University, Evanston, IL (US)

( * ) Notice: Subject to any disclaimer, the term of this patent is extended or adjusted under 35 U.S.C. 154(b) by 0 days.

(21) Appl. No.: 09/784,887

(22) Filed: Feb. 16, 2001

(65) Prior Publication Data

US 2002/0119165 A1 Aug. 29, 2002

Related U.S. Application Data

(63) Continuation of application No. PCT/US99/18736, filed on Aug. 18, 1999.
(60) Provisional application No. 60/096,993, filed on Aug. 18, 1998.

(51) Int. Cl.$^7$ .............................................. A61K 39/245
(52) U.S. Cl. ................................ 424/231.1; 424/204.1; 435/7.1
(58) Field of Search ................ 424/204.1, 143.1, 424/159.1, 231.1; 435/6, 7.1, 5, 69.1; 530/300; 536/23.72

(56) References Cited

U.S. PATENT DOCUMENTS 6,140,467 A * 10/2000 Ware ........................ 530/350

OTHER PUBLICATIONS

Adey et al., 1996, Gene 169:133–134.
Benedict et al., 1999, J. Immunol. 162:6967–6970.
Browning et al., 1995, J. Immunol. 154:33–46.
Crowe et al., 1994, J. Immunol. Methods 168:79–89.
Gillies et al., 1991, Hybridoma 10:347–356.
Golstein et al., 1988, J. Virol. 62:196–205.
Hsu et al., 1997, J. Biol. Chem. 272:13471–13474.
Isola et al., 1989, J. Virol. 63:2325–2334.
Johnson et al., 1989, J. Virol. 63:819–827.
Kay et al., 1993, Gene 128:59–65.
Marsters et al., 1997, J. Biol. Chem. 272:14209–14032.
Mauri et al., 1998, Immunity 8:21–30.
Montgomery et al., 1996, Cell 87:427–436.
Nicola et al., 1996, J. Virol. 70:3815–3822.
Nicola et al., 1997, J. Virol. 71:2940–2946.
Nicola et al., 1998, J. Virol. 72:3595–3601.
Sahu et al., 1996, J. Immunol. 157:884–891.
Sisk et al., 1994, J. Virol. 68:766–775.
Sodora et al., 1991, J. Virol. 63:5184–5193.
Tal–Singer et al., 1994, Virology 202:1050–1053.
Terry–Allison et al., 1998, J. Virol. 72:5802–5810.
Tessier et al., 1991, Gene 98:177–183.
Towbin et al., 1979, Proc. Natl. Acad. Sci. USA. 76:4350–4354.
Whitbeck et al., 1997, J. Virol. 71:6083–6093.
Williams–Abbott et al., 1997, J. Biol. Chem. 272–19451–19456.
Willis et al., 1998, J. Virol. 72:5937–5947.
Geraghty et al. 1998, Science 280:1618–1620.
Eberle et al., 1995, Gene 159:267–272.
Warner et al., 1998, Virology 246:179–189.

* cited by examiner

*Primary Examiner*—Ali R. Salimi
(74) *Attorney, Agent, or Firm*—Morgan, Lewis & Bockius, LLP

(57) ABSTRACT

The invention includes antiherpesviral peptides and method of generating the same.

7 Claims, 8 Drawing Sheets

PEPTIDES FOR INHIBITION OF HERPES SIMPLEX VIRUS ENTRY

CROSS REFERENCE TO RELATED APPLICATIONS

This application is a continuation of international application number PCT/US99/18736, filed Aug. 18, 1999, which claims priority to U.S. Provisional Application No. 60/096,993, filed Aug. 18, 1998, now abandoned.

STATEMENT REGARDING FEDERALLY SPONSORED RESEARCH OR DEVELOPMENT

The invention was made in part using funds obtained from the U.S. Government (National Institutes of Health Grant No. NS36731) and the U.S. government may have certain rights in the invention.

BACKGROUND OF THE INVENTION

Herpes Simplex Virus (HSV) entry into mammalian cells is a complex process requiring interaction of multiple viral envelope proteins with several host cell membrane receptors. Virion glycoproteins, including gB and gC, appear to mediate initial virus binding to cell surface heparan sulfate glycosaminoglycans. However, this attachment is not sufficient to mediate entry, since some cell types such as swine testis (ST) or Chinese hamster ovary (CHO) cells bind HSV but are not susceptible to infection. Entry of virus into cells requires binding of yet other glycoprotein(s) to one or more cell surface receptors. Glycoproteins gD, gB, and the complex formed by gH and gL are believed to act separately or in concert to promote pH-independent fusion of the viral envelope with the cellular membrane.

Herpesvirus entry mediator protein, a cellular protein designated as HveA (also designated HVEM in some literature sources), is a member of the tumor necrosis factor receptor (TNFR) superfamily. This protein has been described as a target cellular receptor capable of mediating post-attachment entry of HSV into host cells. HveA was identified by expression cloning of several HeLa cell products which, when expressed in otherwise nonpermissive CHO cells rendered the CHO cells susceptible to entry by many HSV strains. A recombinant form of HveA (HveA:Fc) blocked HSV-1 entry into CHO cells which were stably transformed to express HveA. Additionally, antibodies to HveA inhibited HSV-1 entry into some susceptible cell types. Furthermore, a recent study suggests that HveA participates not only in entry of free virus into cells but also in cell-to-cell spread of infection. These studies suggest that HveA mediates virus entry into mammalian cells (Terry-Allison et al., 1998, J. Virol. 72:5802–5810; Montgomery et al., 1996, Cell 87:427–436). The HSV protein which mediates HSV binding with HveA has been shown to be glycoprotein D (gD), which binds with a soluble form of HveA, designated HveA(200t) (Whitbeck et al., 1997, J. Virol. 71:6083–6093) in a specific and saturable manner and inhibits binding of HSV to HveA-expressing cells (Nicola et al., 1997. J. Virol. 71:2940–2946; Nicola et al., 1996, J. Virol. 70:3815–3822; Sodora et al., 1991, J. Virol. 63:5184–5193; Sodora et al., 1991, J. Virol. 65:4424–4431; Tal-Singer et al., 1994, Virology 202:1050–1053; Whitbeck et al., 1997, J. Virol. 71:6083–6093).

Several studies suggest that HveA is involved in activation of the host immune response. For example, HveA is predominantly expressed in lymphocyte-rich tissues, and binding of HveA to several members of the TNFR-associated factor (TRAF) family of proteins activates transcriptional regulators such as nuclear factor κB (NF-κB), Jun N-terminal kinase, and AP-1. Moreover, HveA binds to lymphotoxin-alpha (LT-α) and to a membrane-associated protein designated LIGHT. Lymphotoxin-alpha is a cytokine that is sometimes designated tumor necrosis factor β (TNFβ) (Imboden, 1997, In: Medical Immunology, 9th ed., pp. 150–152, Stites et al., eds., Appleton and Lange Press, Stamford, Conn.). The LT-α cytokine molecule mediates an influx of effector cells such as natural killer cells, large granular lymphocytes, and eosinophils which, in turn, mediate antibody-dependent cellular cytotoxicity (ADCC) activity as described in Gillies et al. (1991, Hybridoma 10:347–356), such that binding of LT-α to HveA, a member of the TNFR family, is associated with these immune processes.

LIGHT is a lymphotoxin homolog, and is expressed by T cells upon induction with phorbol 12-myristate 13-acetate (PMA) and a $Ca^{2+}$ ionophore (Mauri et al., 1998, Immunity 8:21–30; Marsters et al., 1997, J. Biol. Chem. 272:14029–14032; Hsu et al., 1997, J. Biol. Chem. 272:13471–13474).

Interestingly, LIGHT competes with HSV gD for binding to HveA, suggesting that gD can modify HveA signaling activities during entry or egress of HSV, thus modulating the immune response of the host. Indeed, a recent study using recombinant proteins expressed in the baculovirus system, demonstrated that among HSV glycoproteins involved in entry, only gD was capable of binding directly with HveA (Whitbeck et al., 1997, J. Virol. 71:6083–6093). Further, Whitbeck et al., supra, demonstrated that fluid-phase gD bound directly and in a specific and saturable manner with HveA at a 2:1 (HveA:gD) molar ratio. This interaction was dependent on the native conformation, but not on N-glycosylation, of gD.

Previous studies implicated gD as an HSV receptor-binding protein. For example, soluble forms of gD ectodomain blocked virus infection of cells as well as expression of gD at the cell surface (i.e., gD-mediated interference). Moreover, UV-inactivated wild type HSV, but not UV-inactivated gD-deficient HSV, were able to inhibit infection (Johnson et al., 1989, J. Virol. 63:819–827). However, three infectious strains of HSV (Rid1, Rid 2 and ANG) which contain point mutations in the gD ectodomain, failed to bind to HveA, suggesting that proteins other than HveA may have a role in HSV entry into cells. Subsequently, two additional cell surface proteins, both members of the immunoglobulin (Ig) superfamily, have been identified which facilitate HSV entry into CHO cells. These proteins are the Poliovirus Receptor Related Protein 1 (HveC, formerly Prr1) and Poliovirus Receptor Related Protein 2 (HveB, formerly Prr2). Moreover, HveA is not the sole receptor for gD; rather, gD has also been identified as the viral ligand for HveC. In contrast to HveB, which enhances entry of a limited number of HSV mutant strains, HveC mediates entry of several alphaherpesviruses (HSV-1, HSV-2 PRV and BHV-1) into cells.

Given the frequency and severity of HSV infections in humans, there is a need to develop compounds which inhibit HSV replication. To date, anti-HSV therapeutics have been directed primarily at inhibiting HSV DNA replication, an event which occurs following entry of the virus into cells. Inhibition of entry of virus into cells prior to DNA replication has significant advantages over therapies directed at events subsequent to virus entry, in that such inhibition guarantees that no progeny virus will be generated (because the virus is rendered incapable of infecting the cell). The present invention provides compounds which inhibit entry of HSV into cells and also provides methods of making such compounds and of using them as inhibitors of HSV entry into cells.

BRIEF SUMMARY OF THE INVENTION

The invention relates to cyclic peptides that bind with HveA and inhibit interaction of HveA with its ligands. Binding of HveA with one or more of the peptides inhibits interaction of the receptor with HSV gD such that virus entry into cells is inhibited. Furthermore, binding of HveA with one or more of the peptides inhibits HveA interaction with LT-α.

Thus, the invention includes a cyclic peptide selected from the group consisting of BP-1, BP-2, and mutants, homologs, derivatives, and variants thereof, wherein the peptide is capable of binding with HveA. In one aspect, the peptide inhibits binding of herpes simplex virus gD with HveA. In another aspect, the peptide is BP-1 and it inhibits binding of lymphotoxin-alpha (LT-α) with HveA. In a further aspect, the peptide inhibits entry of a HSV e.g. HSV-1 or HSV-2, into a cell.

The invention also includes an isolated nucleic acid encoding a cyclic peptide selected from the group consisting of BP-1, BP-2, and mutants, homologs, derivatives, and variants thereof, wherein the peptide binds HveA. In one aspect, the peptide inhibits binding of HSV gD with HveA. In another aspect, the peptide is BP-1, and the peptide inhibits binding of LT-α with HveA.

The invention further includes a method of inhibiting the ability of HveA to bind with HSV gD. The method comprises contacting HveA with a peptide selected from the group consisting of BP-1, BP-2, and mutants, homologs, derivatives, and variants thereof. In one aspect, the peptide is added to a preparation of HSV gD and HveA.

The invention includes a method of inhibiting entry of an HSV into a cell. The method comprises contacting a cell with a peptide selected from the group consisting of BP-1, BP-2, and mutants, homologs, derivatives, and variants thereof. The peptide binds with cellular HveA and inhibits binding of HSV gD with cellular HveA, thereby inhibiting entry of the HSV into the cell. In one aspect, the cell is contacted with the peptide in the presence of HSV gD.

The invention also includes a method of inhibiting replication of an HSV. The method comprises contacting a cell with a peptide selected from the group consisting of BP-1, BP-2, and mutants, homologs, derivatives, and variants thereof. The peptide binds with cellular HveA, thereby inhibiting binding of HSV gD with the HveA and inhibiting replication of the HSV. In one aspect, the cell is contacted with the peptide in the presence of HSV gD.

The invention includes a method of treating a human infected with an HSV. The method comprises administering to the human a peptide in a pharmaceutically acceptable carrier. The peptide is selected from the group consisting of BP-1, BP-2, and mutants, homologs, derivatives, and variants thereof. The peptide binds with HveA thereby treating the human infected with the HSV.

The invention also includes a method of producing a cyclic peptide which affects interaction between HSV gD and an HSV receptor protein which binds gD. The method comprises (a) preparing a random peptide phage display library;
(b) selecting phage that bind to either of HSV gD and HveA;
(c) isolating the phage; and
(d) isolating the peptide from the isolated phage. A peptide which affects the interaction between HSV gD and the HSV receptor proteins is thereby provided. The invention further includes a cyclic peptide produced by this method. In one aspect, the HSV receptor protein is selected from the group consisting of HveA, HveB, and HveC.

The invention further includes a cyclic peptide selected from the group consisting of BP-1, a fragment thereof, and a variant thereof, wherein the peptide binds with HveA. The peptide also inhibits binding of LT-α with HveA.

The invention also includes a method of inhibiting binding of HveA with LT-α. This method comprises combining a peptide and a preparation of LT-α and HveA. The peptide is selected from the group consisting of BP-1, a fragment thereof, and a variant thereof. The peptide binds with at least one of LT-α and Hve A and inhibits binding of HveA with LT-α.

The invention includes another method of inhibiting binding of HveA with LT-α. This method comprises contacting HveA with a peptide selected from the group consisting of BP-1, a fragment thereof, and a variant thereof. The peptide binds with HveA, and inhibits binding of HveA with LT-α.

The invention includes a method of producing a cyclic peptide which affects interaction between LT-α and HveA. The method comprises (a) preparing a random peptide phage display library;
(b) selecting a phage that binds with at least one of LT-α and HveA;
(c) isolating the phage; and
(d) producing a cyclic peptide from the isolated phage, thereby producing a cyclic peptide which affects interaction between LT-α and HveA.

The invention also includes a method of determining whether a test compound affects HSV gD binding with HveA. According to this method, a first preparation is made comprising a surface having at least a portion of HveA bound thereon, the test compound, and a suspension of a phage in contact with the surface. The phage displays a cyclic peptide selected from the group consisting of BP-1 and BP-2, and mutants, homologs, derivatives, and variants of BP-1 and BP-2. The amount of phage bound with the surface in the first preparation is assessed. This amount is compared with the amount of phage bound with the surface in an otherwise identical preparation to which the test compound is not added. A difference between the amount of phage bound with the surface in the first preparation with the otherwise identical preparation is an indication that the test compound affects the binding of gD with HveA. In one aspect, the amount of phage bound with the surface is assessed using an antibody that specifically binds with the phage.

The invention includes another method of determining whether a test compound affects HSV gD binding with HveA. According to this method, a first preparation is made comprising a surface having at least a portion of HveA bound thereon, the test compound, and a cyclic peptide selected from the group consisting of BP-1 and BP-2, and mutants, homologs, derivatives, and variants of BP-1 and BP-2, in contact with the surface. The amount of the peptide bound with the surface in the first preparation is assessed. This amount is compared with the amount of the peptide bound with the surface in an otherwise identical preparation to which the test compound is not added. A difference between the amount of peptide bound with the surface in the first preparation with the otherwise identical preparation is an indication that the test compound affects the binding of gD with HveA.

The invention also includes a method of determining whether a test compound affects LT-α binding with HveA. According to this method, a first preparation is made comprising a surface having at least a portion of HveA bound thereon, the test compound, and a suspension of a phage in contact with the surface. The phage displays BP-1. The amount of phage bound with the surface in the first preparation is assessed. This amount is compared with the amount of phage bound with the surface in an otherwise identical preparation to which the test compound is not added. A difference between the amount of phage bound with the surface in the first preparation with the otherwise identical preparation is an indication that the test compound affects the binding of LT-α with HveA.

The invention includes another method of determining whether a test compound affects LT-α binding with HveA. According to this method, a first preparation is made comprising a surface having at least a portion of HveA bound thereon, the test compound, and a BP-1 peptide in contact with the surface. The amount of the BP-1 peptide bound with the surface in the first preparation is assessed. This amount is compared with the amount of the BP-1 peptide bound with the surface in an otherwise identical preparation to which the test compound is not added. A difference between the amount of BP-1 peptide bound with the surface in the first preparation with the otherwise identical preparation is an indication that the test compound affects the binding of LT-α with HveA. In one aspect, the BP-1 peptide is labeled.

DETAILED DESCRIPTION OF THE INVENTION

Figure 2:
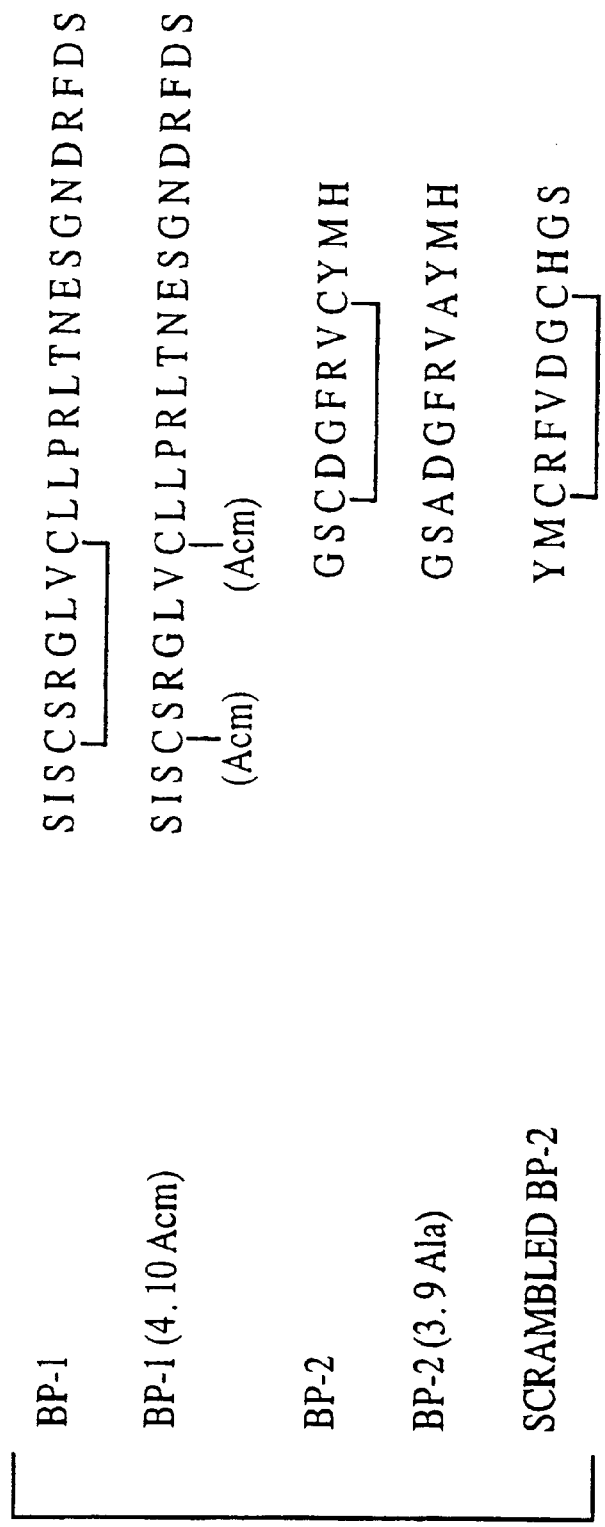
FIG. 2 depicts the structures of HveA-binding peptides BP-1 (SEQ ID NO:4), and BP-2 (SEQ ID NO:5), and their variants BP-1 (4, 10 Acm) (SEQ ID NO:1), BP-2 (3, 9 Ala) (SEQ ID NO:2), and scrambled BP-2 (SEQ ID NO:6). The lines connecting the cysteine residues in these structures represent disulfide bonds.

The present invention relates to two cyclic HveA-binding peptides (herein designated BP-1 and BP-2) which affect interaction of cellular HveA with herpes simplex virus gD and which, in turn, can inhibit HSV entry into cells. As more fully set forth below, HveA was used to screen two phage-displayed random peptide libraries. The structures of these two cyclic peptides are depicted in FIG. 2. BP-1 and BP-2 bind with HveA and distinctly inhibit the binding-of herpes simplex virus (HSV) glycoprotein D (gD) with HveA. Moreover, BP-2 blocks HSV entry into HveA-expressing cells.

It has been discovered that the cyclic peptides of the invention (i.e., BP-1 and BP-2) affect interaction of HveA with its ligands. For instance, BP-2 inhibits HveA binding with HSV gD. BP-1 inhibits HSV gD binding with HveA to a lesser extent than BP-2. BP-1 also inhibits LT-α binding with HveA; BP-2 has no detectable effect on HveA/LT-α interaction. The cyclic peptides of the invention therefore are useful for inhibiting HSV entry into cells and also are useful for development of additional compositions (e.g. mutants, homologs, derivatives, and variants of the cyclic peptides of the invention and nucleic acids encoding them) which block the interaction between HveA, its natural ligands, and virus specific protein(s) involved in HSV entry into cells. Thus, the invention provides novel compositions and methods of antiviral therapy, immunomodulation, or both.

BP-1 is a cyclic 26-residue peptide that inhibits binding of gD with HveA. BP-1 also blocks binding of HveA with one of its natural ligands, LT-α. Moreover, preventing disulfide bond formation by blocking the cysteine groups of BP-1 using an acetamidomethyl (Acm) group, i.e., thereby producing BP-1 (4, 10 Acm), destroyed the ability of BP-1 to inhibit binding of HveA with HSV gD or with LT-α.

BP-2 is a cyclic 12-residue peptide that inhibits binding of HSV gD with HveA and which blocks HSV entry into CHO-HveA cells. Unlike BP-1, BP-2 does not inhibit HveA binding to LT-α. However, linearization of BP-2 (e.g., by alanine substitution of the two cysteine residues of BP-2 to yield BP-2 (3, 9 Ala), abrogates the ability of BP-2 to bind HveA or to inhibit gD binding with HveA. These results suggest that BP-1 and BP-2 interact with HveA to block HSV entry into CHO-HveA cells and to affect the host immune response to HSV infection mediated by binding of LT-α with HveA. Therefore, these peptides, as well as mutants, homologs, derivatives, and variants of these peptides, are important therapeutics to combat herpesvirus infection and to inhibit disorders associated with aberrant cytokine activity of LT-α.

The invention includes a cyclic peptide selected from the group consisting of BP-1, BP-2, and mutants, homologs, derivatives, and variants thereof, which binds with cellular HveA, thereby disrupting binding of HSV gD with cellular HveA, an important mediator of HSV entry into cells. The peptides of the invention are useful for inhibiting entry of HSV into cells and are therefore useful anti-herpesvirus therapeutic compounds, as are the mutants, homologs, derivatives, and variants thereof.

The invention includes inhibition of entry of HSV-1 and HSV-2 into cells and also includes inhibition of entry of other alpha-herpesviruses into cells using other peptides generated by following the protocols disclosed herein. Preferably, the virus the entry of which into cells is inhibited is HSV-1.

The cyclic peptides of the invention block, inter alia, the interactions between an HSV gD, and a host cell protein, HveA. However, the invention is not limited to HSV gD as the ligand or to HveA as the receptor. Instead, the invention encompasses other ligand and receptor combinations that interact with the peptides of the invention in a similar manner to the interaction of HveA with the cyclic peptides of the invention. Other cell receptors having homology with HveA also bind BP-1, BP-2, or both, such that the cyclic peptides of the invention abrogate binding of ligands with such receptors. Therefore, the present invention includes inhibition of ligand/receptor interactions involving receptors which are homologous with HveA. Once homology between HveA and a putative TNFR-like protein is established (e g., by searching DNA or protein databases such as GenBank or SwissProt), the methods disclosed herein are used to determine whether a cyclic peptide of the invention inhibits binding of the homologous receptor and its ligand(s).

A TNFR family member having substantial homology with HveA was recently identified by Benedict et al. (1999, J. Immunol. 162:6967–6970). Benedict et al., identified a non-cellular structural homolog of HveA encoded by the UL144 open reading frame of human cytomegalovirus (HCMV). ClustalW analysis of amino acid sequence homology indicated 46% homology between HveA and HCMV UL144. The cyclic peptides of the invention can also inhibit UL144 interaction(s) with various ligands, which interactions can be required for one or more of virus (e.g., HCMV) entry, immune evasion, blockade of apoptosis, and maintenance and spread of virus infection. Therefore, the cyclic peptides of the invention are useful therapeutics to treat and inhibit infection by pathogens which interact with one or more members of the TNFR superfamily (e.g., Fas, TNFR-1, LTβR, or TRAIL-R2) or TNF-related ligands (e.g., TRAIL, LIGHT, LT-α, LT-α1β2, TNF, FasL, CD40L, CD30L, Tweak, 41BBL, OX40L, April, RankL, or TL1).

The invention includes a cyclic peptide selected from the group consisting of BP-1, BP-2, and mutants, homologs, derivatives, and variants thereof. Preferably, the amino acid sequence of the isolated peptide is at least about 50% homologous to the amino acid sequence of at least one of BP-1 (SEQ ID NO:4) and BP-2 (SEQ ID NO:5). More preferably, the isolated peptide is at least about 60%, 70%, 80%, 90%, 95%, or 99% homologous with at least one of the amino acid sequences of BP-1 (SEQ ID NO:4) and BP-2 (SEQ ID NO:5). More preferably, the isolated peptide is one of BP-1 and BP-2.

It is not necessary that the cyclic peptide of the invention comprise the full complement of amino acids recited above. Rather the peptide of the invention may comprise less than the full length of either of the peptides recited above. For example, the peptide may comprise about five amino acids, preferably about ten amino acids and, even more preferably about twelve or more amino acids in length. It is merely necessary that the peptide be capable of disrupting the interaction of HSV gD with HveA or LT-α in one of the assays provided herein.

The cyclic peptides of the invention can have at least one amino acid residue at either one or both ends. For example, the peptides can have 1, 2, 3, 4, 5, 10, or 20, or more amino acid residues at either the amino or carboxyl terminus, or at both termini.

The cyclic peptides of the invention can be obtained by any suitable means including, but not limited to, synthetic means, recombinant means, biochemical means, and the like. The generation of peptides is well known in the art and is described, for example, in Sambrook et al. (1989, Molecular Cloning: A Laboratory Manual, Cold Spring Harbor Laboratory, New York), and in Ausubel et al. (1993, Current Protocols in Molecular Biology, Green & Wiley, New York).

The invention includes a nucleic acid encoding a cyclic peptide of the invention. Such nucleic acid can also be obtained by any suitable means, including, but not limited to, synthetic means and recombinant means. In one embodiment, a nucleic acid encoding BP-1 has the nucleic acid sequence 5'-TCTATTTCCTGCTCTAGGGGGTTA GTTTGCCTCTTACCGCGATTGACTAACGAG TCCGGTAATGATAGGTTCGACTCT-3' (SEQ ID NO:7), and a nucleic acid encoding BP-2 has the nucleic acid sequence 5'-GGGTCGTGTGATGGGTTTAGGGTGTGT TATATGCAT-3' (SEQ ID NO:8). However, the nucleic acid of the present invention is not limited to these nucleic acid sequences. Instead, the present invention includes any nucleic acid sequence encoding BP-1, BP-2, or a mutant, homolog, derivative, or variant thereof.

Generation of, for example, DNA encoding specific peptides is well known in the art and is described, for example, in Sambrook et al. (1989, Molecular Cloning: A Laboratory Manual, Cold Spring Harbor Laboratory, New York) and in Ausubel et al. (1993, Current Protocols in Molecular Biology, Green & Wiley, New York). DNA encoding a cyclic peptide of the invention may be cloned and expressed in any suitable expression vector and may further be operably linked to any suitable promoter/regulatory sequence in order that the DNA is expressed in a desired cell.

Upon reading the present disclosure, the skilled artisan is able to generate mutants, homologs, derivatives, and variants of the cyclic peptides of the invention, or of DNA encoding the same, which peptides have the property of binding to cellular HveA, and disrupting binding of HSV gD with cellular HveA. Such technology is also described in Sambrook et al. (1989, Molecular Cloning: A Laboratory Manual, Cold Spring Harbor Laboratory, New York) and in Ausubel et al. (1993, Current Protocols in Molecular Biology, Green & Wiley, New York).

Homologs of the peptides of the invention are peptides which share significant amino acid sequence homology with BP-1 and BP-2, and which have the property of binding with cellular HveA. Such homologs can disrupt binding of HSV gD, LT-α, or both, with HveA.

In another aspect, the present invention includes a nucleic acid encoding a cyclic peptide wherein the peptide encoded by the nucleic acid has at least about 50% amino acid sequence homology with BP-1 or with BP-2. Preferably, the peptide encoded by the nucleic acid is about 60%, 70%, 80%, 90%, 95%, or 99% homologous with BP-1 or BP-2. More preferably, the peptide encoded by the nucleic acid is BP-1 or BP-2.

"Mutants," "derivatives," and "variants" of the cyclic peptides of the invention (or of the DNA encoding the same) are cyclic peptides which are altered at one or more amino acid residues (or at one or more nucleotide residues) such that the peptide (or nucleic acid) is not identical to the sequences corresponding to BP-1 or BP-2 recited herein, but has the same property as the peptides disclosed herein, in that the peptide has the property of binding to cellular HveA. Derivatives may, for example, have substituent moieties pending from one or more amino acid residues.

The peptides of the invention can be isolated or even substantially pure. A substantially pure peptide can be purified using known procedures for protein purification, wherein an immunological, enzymatic, or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The present invention also provides for variants of the peptides of cyclic the invention. Variants can differ from BP-1 or BP-2 by conservative amino acid sequence differences or by modifications which do not affect sequence, or by both. For example, conservative amino acid changes may be made, which although they alter the primary sequence of the peptide, do not alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

Modifications (which do not normally alter primary sequence) include in vivo, or in vitro chemical derivatization of peptides, e.g., acetylation or carboxylation. Also included are modifications of glycosylation, e.g., those made by modifying the glycosylation patterns of a peptide during its synthesis and processing or in further processing steps; e.g., by exposing the peptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are cyclic peptides which have been modified using ordinary molecular biological techniques so as to improve their resistance to proteolytic degradation or to optimize solubility properties or to render them more suitable as a therapeutic agent. Analogs of such peptides include those containing residues other than naturally occurring L-amino acids, e.g., D-amino acids or non-naturally occurring synthetic amino acids. The cyclic peptides of the invention are not limited to products of any of the specific exemplary processes listed herein.

The invention includes a method of inhibiting entry of HSV into a cell. Interaction between HSV gD and a cellular HveA receptor is required for virus entry into the susceptible cell. Inhibiting this interaction inhibits entry of the virus into the cell.

Further, the present invention includes a method of inhibiting replication of HSV. This is because, inhibition of entry of HSV into a cell necessarily prevents virus replication which requires entry of HSV into the host cell.

In addition, the invention includes a method of treating a human infected with HSV. HveA is involved not only in initial entry of HSV into a cell (i.e., to initiate infection), but is also involved in the cell-to-cell spread of HSV infection. Inhibition of interaction of gD with HveA inhibits virus entry, as well as virus spread from infected cells to adjacent uninfected cells. Inhibition of virus entry and of cell-to-cell spread is an effective treatment for virus infection, preventing infection and decreasing the rate, the magnitude, or both, of infection. The method comprises administering to a human (e.g., a human infected with an HSV) a cyclic peptide of the invention, or a nucleic acid encoding the same. The cyclic peptide or nucleic acid encoding the peptide can be suspended in a pharmaceutically acceptable carrier.

The invention also includes a method of generating peptidometics and small molecules which are based upon the sequence of the two peptides exemplified herein (i.e., BP-1 and BP-2), which peptidometics and small molecules have the property of binding to cellular HveA and disrupting binding of HSV gD with HveA. Generation of peptidometics can be accomplished using techniques described in PCT/US93/01201 and in U.S. Pat. No. 5,334,702, for example. Generation of small molecules can be accomplished by first identifying contact points between a cyclic peptide of the invention and HveA and then synthesizing small molecules which are specifically designed to mimic binding of the peptide with HveA.

The invention also includes a method of producing a cyclic peptide and nucleic acid encoding the same. The cyclic peptide has the property of binding with HveA and affecting interaction of gD and HveA. The method comprises preparing a random peptide phage display library, binding one or more of the phage with either of gD and HveA (e.g., gD or HveA bound at a surface), isolating phage which so bind and isolating DNA or peptide from those phage. In this manner, the cyclic peptide is produced. The cyclic peptide has the property of binding to cellular HveA, thus affecting interaction of gD and cellular HveA. Nucleic acid encoding the peptide displayed by a phage of the library is contained within the phage. Thus, both the peptide and a nucleic acid encoding it can be co-isolated.

The invention further includes a method of producing a cyclic peptide and a DNA encoding it. The peptide is capable of disrupting binding of gD with cellular virus receptor proteins, such as, but not limited to, HveB and HveC. This method of the invention is performed in a similar manner to that described above, substituting the desired cellular virus receptor protein in place of HveA.

The invention also includes a method of producing a cyclic peptide and a nucleic acid encoding the same. The cyclic peptide has the property of binding with HveA and disrupting binding of LT-α with HveA (e.g., on a cell surface). The method comprises preparing a random peptide phage display library, binding the phage with either of LT-α or HveA (e.g., on a surface), isolating phage which so bind, and isolating DNA or peptide from phage which bind. A peptide and a DNA molecule encoding it are produced.

Also included in the invention is a method of inhibiting interaction of HSV gD with cellular HveA. This method comprises contacting a cyclic peptide selected from the group consisting of BP-1, BP-2, and mutants, homologs, derivatives, and variants of either of these, with the cellular HveA. The peptide binds with HveA and disrupts interaction of HveA with gD. In one aspect, the method comprises adding the cyclic peptide to a preparation comprising both HSV gD and cellular HveA. The peptide binds with HveA and disrupts interaction of gD with HveA. For example, the preparation may comprise an HSV having gD on the surface thereof (e.g., HSV-1 or HSV-2) and a cell having HveA on its surface. The HSV is capable of infecting the cell. However, if a cyclic peptide of the invention is added to the preparation, then the virus is no longer able to infect the cell because the peptide inhibits binding of HSV gD with cellular HveA, thereby inhibiting entry of the HSV into the cell. The present invention is not limited to adding the peptide of the invention to a preparation in which both HveA and gD are present. Addition of a cyclic peptide of the invention to any preparation comprising HveA causes the peptide to bind with HveA such that binding between HveA and gD is inhibited.

Also included in the invention is a method of inhibiting the interaction of LT-α with HveA (e.g. HveA on the surface of a cell). This method comprises combining a cyclic peptide of the invention with a preparation comprising HveA. The cyclic peptide of the invention binds with HveA and inhibits interaction between HveA and LT-α, regardless of whether HveA and LT-α are bound at the time. The present invention is not limited to addition of the peptide of the invention to preparations comprising both HveA and LT-α. The peptide can be combined with HveA either before, during, or after interaction between HveA and LT-α has occurred.

The invention includes a method of treating a human having an HSV infection. The method comprises administering to the human a cyclic peptide of the invention, or a nucleic acid encoding a cyclic peptide of the invention (e.g., a nucleic acid contained in a vector). The peptide or nucleic acid can be suspended in a pharmaceutically acceptable carrier.

Administration of peptides and/or nucleic acids to humans is well known in the art and formulations and preparations for such administration and dosages of the same are within the ken of the ordinarily skilled artisan.

The invention encompasses use of pharmaceutical compositions comprising a cyclic peptide of the invention, a nucleic acid encoding a cyclic peptide of the invention, or both, suspended in a pharmaceutically-acceptable carrier.

The pharmaceutical compositions useful for practicing the invention may be administered to deliver a dose of peptide, nucleic acid, or nucleic acid vector between 1 nanogram per kilogram per day and 100 milligrams per kilogram per day.

Pharmaceutical compositions that are useful in the methods of the invention may be administered systemically in oral solid formulations, ophthalmic, suppository, aerosol, topical, or other similar formulations. In addition to the peptide or nucleic acid of the invention, such pharmaceutical compositions can contain pharmaceutically-acceptable carriers and other ingredients known to enhance and facilitate drug administration. Other possible formulations, such as nanoparticles, liposomes, resealed erythrocytes, and immunologically based systems may also be used to administer the nucleic acid or peptide according to the methods of the invention.

The invention includes a method of identifying a test compound that affects HSV gD binding with HveA. The method comprises making a first preparation comprising HveA, the test compound, and at least one phage displaying a peptide capable of inhibiting binding of gD with HveA such as, but not limited to, BP-1 and BP-2. The phage or HveA may be bound at a surface. Binding of HveA with the phage in the first preparation is compared with binding of HveA with phage in an otherwise identical preparation which does not contain the test compound. Binding of the phage with HveA can, for example, be determined as disclosed herein; that is, HveA immobilized on a surface is incubated with phage and phage bound to the surface are detected using an antibody which binds specifically with the phage including, but not limited to, an antibody which binds specifically with bacteriophage M13. Such antibody can be labeled antibody or can be detected using a labeled secondary antibody. A difference between the amount of phage bound with HveA in the first preparation and the amount of phage bound with HveA in the otherwise identical preparation is an indication that the test compound affects gD binding with HveA.

HveA can be immobilized on a solid support, such as a well of a plastic microtiter plate. Recombinant HveA containing a "tag" epitope may be immobilized on a resin which binds the tag. Such tag epitopes and resins which specifically bind them are well known in the art and include, for example, tag epitopes comprising a plurality of sequential histidine residues, which allows isolation of a chimeric protein comprising such an epitope on nickel-nitrilotriacetic acid-agarose, a hemagglutinin (HA) tag epitope allowing a chimeric protein comprising such an epitope to bind with an anti-HA-monoclonal antibody affinity matrix, a glutathione-S-transferase tag epitope, and a maltose binding protein (MBP) tag epitope, which can induce binding between a protein comprising such an epitope and a glutathione- or maltose-Sepharose column, respectively. Production of proteins comprising such tag epitopes is well known in the art and is described in standard treatises such as Sambrook et al., 1989, and Ausubel et al., supra.

The data disclosed herein demonstrate that binding of HveA with phage displaying a cyclic peptide of the invention provides a sensitive system for identifying a compound (e.g., a cyclic peptide) that affects gD binding with HveA. This method can also be used to assess whether a test compound affects binding of gD with HveA. Binding of phage-displayed peptide with HveA correlates with binding of gD with HveA, as the data disclosed herein demonstrate. That is, the phage-displayed peptides disclosed herein were selected for their ability to bind with HveA. Peptides isolated from such phage were able to inhibit gD binding with HveA. Therefore, a substance which affects binding of a phage, or a peptide isolated from a phage, with HveA also affects binding of gD with HveA because binding of the peptide with HveA is analogous to binding of HveA with its natural ligand.

The invention also includes a method of identifying a test compound that affects LT-α binding with HveA. The method comprises making a first preparation comprising HveA (preferably immobilized on a surface), the test compound, and at least one phage displaying a peptide capable of inhibiting binding of LT-α with HveA. Such peptides include, but are not limited to, cyclic peptides of the invention, such as BP-1. The phage is capable of contacting the surface (e.g., because the surface contacts a phage suspension). The amount of phage bound with the surface in the first preparation (i.e., containing the test compound) is compared with the amount of phage bound with the surface in an otherwise identical preparation which does not contain the test compound. The binding of the phage with the surface may be determined as disclosed herein (e.g., an antibody which specifically binds with the phage). A difference between the amount of phage bound with the surface in the first preparation and in the amount of phage bound with the surface in the otherwise identical preparation is an indication that the test compound affects LT-α binding with HveA.

The data disclosed herein demonstrate that binding of phage displaying BP-1 with HveA provides a sensitive system for identifying a compound (e.g., a cyclic peptide such as a variant BP-1) that affects LT-α binding with HveA. Binding of phage-displayed peptide with HveA correlates with the binding of LT-α with HveA, as the data disclosed herein demonstrate. Phage-displayed peptides were selected for their ability to induce binding of the phage with HveA. The peptides isolated from HveA-binding phage were able to inhibit LT-α binding with HveA. Therefore, a substance which affects binding of a phage displaying BP-1, or binding of BP-1, with HveA affects binding of LT-α with HveA. This is so because binding of a peptide with HveA is analogous to binding of HveA with LT-α, a natural ligand of HveA.

Inhibition of interaction between HveA and LT-α is useful for preventing, alleviating, and treating various disease conditions associated with interaction of LT-α and HveA. LT-α is a cytokine that is involved in autoimmune tissue damage. Therefore, blocking or inhibiting the interaction of LT-α with HveA can prevent, inhibit, ameliorate, or reverse pathology associated with one or more autoimmune diseases. Indeed, amelioration of autoimnmune disease has been successfully achieved in vivo. Blocking of either TNF or LT-α using neutralizing antibodies in three animal models of autoimmune disease (i.e., rheumatoid arthritis, experimental autoimmune encephalomyelitis, and experimental autoimmune uveoretinitis) ameliorated the disease. Therefore, BP-1 is useful as a therapeutic in LT-α-mediated tissue damage in autoimmune diseases, as are mutants, homologs, derivatives, and variants of BP-1. Because BP-2 and its mutants, homologs, derivatives, and variants also interfere with binding between HveA and ligands thereof (e.g., HSVs), these agents are also useful for prevention, inhibition, amelioration, and reversal of HveA-associated diseases.

In addition, studies of the in vivo function of LT-α employing gene targeting technology have demonstrated that LT-α has a central role in formation of secondary lymphoid organs during development. LT-α also controls formation of germinal centers necessary for immunoglobulin-isotype switching during immune responses in adults. Soluble LT-α interacts with two receptors, designated TNFRI and TNFRII, which are expressed in most cell types. Interaction of LT-α with one or both of these receptors can lead to cellular cytotoxicity, induction of host defense (antiviral and antibacterial) mechanisms, and thymocyte proliferation. Thus, BP-1 is useful as a potential regulator of these physiological processes.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, to "alleviate" a HSV infection means reducing the severity of one or more symptoms associated with the infection.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

By the terms "encoding" and "coding," as these terms are used herein, is meant that the nucleotide sequence of a nucleic acid is capable of specifying a particular polypeptide of interest. That is, the nucleic acid may be transcribed or translated, or both, to produce the polypeptide. Thus, for example, a nucleic acid encoding BP-1 is capable of being transcribed and translated to produce BP-1. The use of the terms "nucleic acid encoding" or "nucleic acid coding" should be construed to include the RNA or DNA sequence which encodes the desired protein and any necessary 5' or 3' untranslated regions accompanying the actual coding sequence.

As used herein, the term "fragment" as applied to a polypeptide, means at least about 5, 10, 15, 20, 30, or 40 or more contiguous amino acid residues of the polypeptide from which the fragment is derived.

By the term "cellular HveA," as used herein, is meant a protein having the amino acid sequence of herpesvirus entry mediator protein (formerly named HVEM) as described in Montgomery et al. (1996, Cell 87:427–426), wherein the protein is associated with a cell. Preferably, the protein is present on the cell surface or is otherwise accessible to binding with the peptides of the invention and/or with its natural ligands, e.g., HSV gD, LIGHT, and LT-α.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGCG 5' share 50% homology. Any of a variety of known algorithms may be used to calculate the percent homology between two nucleic acids or two proteins of interest and these are well-known in the art.

By the term "isolated nucleic acid," as used herein, is meant a nucleic acid sequence, or a fragment thereof, which has been separated from the sequences which flank it in a naturally occurring state, e.g., a DNA fragment which has been removed from the sequences which are normally adjacent to the fragment (e.g., the sequences adjacent to the fragment in a genome in which it naturally occurs). The term also applies to nucleic acids which have been substantially purified from other components (e.g., RNA or DNA or proteins), which naturally accompany the nucleic acid in the cell. The term therefore includes, for example, a recombinant DNA which is incorporated into a vector; into an autonomously replicating plasmid or virus; or into the genomic DNA of a prokaryote or eukaryote; or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequences.

By the terms "isolated peptide," "isolated polypeptide," or "isolated protein," as used herein, is meant a peptide or protein which has been substantially separated from the components (e.g., DNA, RNA, other proteins and peptides, carbohydrates and lipids) which naturally accompany the protein or peptide in the cell. The terms isolated peptide and protein include a peptide or protein which is expressed and/or secreted from a cell comprising an isolated nucleic acid.

A "cyclic" peptide" has two cysteines residues or other residues that can be cross-linked, optionally using a cross-linking agent (e.g., a carbodiimide). It is understood that a peptide having two or more sulfhydryl groups may be maintained (eg., under reducing conditions in a linear form), the cyclic form of the peptide being formed upon exposure to oxidizing conditions or cross-linking agent. Thus, a cyclic peptide of the invention may be maintained in linear form prior to use.

"Mutants," "derivatives," and "variants" of a cyclic peptide of the invention (or of a nucleic acid encoding the same) are peptides which are altered at one or more amino acid residues (or at one or more nucleotide residues) such that the peptide (or nucleic acid) is not identical to the sequence corresponding to BP-1 or BP-2, but has the same property as BP-1 or BP-2, in that the peptide binds with HveA and inhibits binding of gD or LT-α with HveA.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, the term "pharmaceutically-acceptable carrier" means a chemical composition with which a peptide, a nucleic acid encoding the peptide, or a vector comprising such a nucleic acid, may be combined and which, following the combination, can be used to administer the protein, the nucleic acid encoding the peptide, or the vector comprising such a nucleic acid, to a patient.

"Polypeptide" and "peptide" are used interchangeably to refer to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. Conventional notation is used herein to portray polypeptide sequences: the left-hand end of a polypeptide sequence is the amino-terminus; the right-hand end of a polypeptide sequence is the carboxyl-terminus.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A protein (e.g., an antibody) or a nucleic acid "specifically binds with" a particular molecule if the protein or nucleic acid recognizes and binds with the particular molecule (e.g., a protein or a nucleic acid), but does not substantially recognize or bind other molecules in a sample.

As used herein, the term "substantially pure" describes a compound, e.g., a nucleic acid, protein or polypeptide, which has been separated from components which naturally accompany it. Typically, a compound is substantially pure when at least about 10%, 20%, 50%, 75%, 90%, or 99% of the total material (by volume, by wet or dry weight, or by mole percent or mole fraction) in a sample is the compound of interest. Purity can be measured by any appropriate method (e.g., by column chromatography, gel electrophoresis, or HPLC analysis).

A compound (e.g., a nucleic acid, a protein, or a peptide) is also "substantially purified" when it is essentially free of naturally associated components or when it is separated from the native contaminants which accompany it in its natural state. Thus, a "substantially pure" preparation of a nucleic acid, as used herein, refers to a nucleic acid sequence which has been purified from the sequences which flank it in a naturally occurring state (e.g., a DNA fragment which has been removed from the sequences which are normally adjacent to the fragment in a genome in which it naturally occurs).

The invention is further described in detail by reference to the following experimental examples. These examples are provided for purposes of illustration only, and are not limiting. Thus, the invention is not limited to the following examples, but rather, encompasses variations which are evident as a result of the teaching provided herein.

EXAMPLE 1

Novel Peptides which Bind HveA and Affect its Binding with other Ligands and Block HSV Entry into Cells in vitro Several cellular receptors of HSV have been described which mediate viral entry into the cell following attachment of the virus to the cell. The first one to be characterized was HveA, a member of the TNF receptor family, which facilitates entry of most HSV strains into non-permissive CHO cells. This process is mediated by direct binding of HSV gD with HveA.

The present invention discloses two cyclic peptides (BP-1 and BP-2) identified by screening two different phage-displayed random peptide libraries to identify peptides which bind with HveA. HveA-binding peptides can affect interaction of HveA with gD and can, therefore, inhibit HSV entry into cells. The data disclosed herein enhance understanding of the process of viral entry at the level of the interaction between gD and HveA, and of interaction of HveA with two of its ligands, LT-α and LIGHT.

The Materials and Methods used in the experiments presented in this example are now described.

Chemicals and Buffers

All chemicals and reagents used for peptide synthesis were purchased from Applied Biosystems, Inc. (Foster City, Calif.) with the exception of F-moc (9-fluorenylmethoxycarbonyl) amino acids, which were obtained from Nova Biochem (San Diego, Calif.).

Production and Purification of Soluble Forms of HveA (200t) gD-1(306t), and gD-1(Δ290–299t)

Production and purification of HveA(200t), gD-1(306t), and gD-1(Δ290–299t), and LT-α from recombinant baculovirus-infected cells have been described (Crowe et al., 1994, J. Immunol. Methods 168:79–89; Nicola et al., 1998. J. Virol. 72:3595–3601; Nicola et al., 1996, J. Virol. 70:3815–3822; Whitbeck et al., 1997, J. Virol. 71:6083–6093; Tessier et al., 1991, Gene 98:177–183; Sisk et al., 1994, J. Virol. 68:766–775; Williams-Abbott et al., 1997, J. Biol. Chem. 272:19451–19456). Briefly, cDNA encoding each protein was amplified by polymerase chain reaction (PCR), five or six terminal histidine codons were added, and a stop codon was also added to the downstream carboxy-terminal primer. The histidine codons were added to provide a binding site for nickel-nitrilotriacetic acid-agarose resin in order to facilitate purification of the encoded protein. PCR-amplified products were cloned into pVT-Bac vector (Tessier et al., 1991, Gene 98:177–183), which encodes the honeybee mellitin signal sequence, and which replaced the signal sequence in each protein.

The resulting constructs were recombined into baculovirus (*Autographa californica* nuclear polyhedrosis virus) vectors by co-transfection of cell with Baculogold DNA (Pharmingen, San Diego, Calif.) and the constructs. Recombinant plaques were isolated and amplified, and the resulting culture supernatants were screened for expression of protein by sodium dodecyl sulfate-polyacrylamide gel electrophoresis (SDS-PAGE; Laemmli, 1970, Nature 227:680–685) and Western blotting (Towbin et al., 1979, Proc. Natl. Acad. Sci. USA. 76:4350–4354). Recombinant baculovirus clones expressing a protein of interest were subjected to two more additional rounds of plaque purification.

*Spodoptera frugiperda* Sf9 cells (GIBCO BRL, Gaithersburg, Md.) were grown in 3-liter suspension cultures and infected at a multiplicity of infection (MOI) of 4. About 48 to 72 hours post-infection, the supernatants of these cultures were cleared by centrifugation, concentrated, and then exchanged into phosphate-buffered saline (PBS). The proteins were affinity-purified using a column containing nickel-nitrilotriacetic acid-agar resin and increasing concentrations of imidazole (0.01 to 0.25 molar) in 0.02 molar phosphate buffer (pH 7.5) containing 0.5 molar NaCl. Eluates were dialyzed against PBS and concentrated.

Antibodies

A polyclonal antibody (R140), which binds specifically with HveA, was generated using a baculovirus form of HveA (200t) in Cocalico rabbits, as described (Terry-Allison et al., 1998, J. Virol. 72:5802–5810; Whitbeck et al., 1997, J. Virol. 71:6083–6093).

R7 antiserum was raised against gD-2 isolated from virus-infected cells as described (Isola et al., 1989, J. Virol. 63:2325–2334).

The production of a monoclonal antibody which binds specifically with LT-α (AG9) was described by Browning et al. (1995, J. Immunol. 154:33–46).

Cells and Viruses

CHO cells were grown in Ham's F-12 medium supplemented with 10% (v/v) fetal bovine serum (FBS). CHO-K1 cells expressing HveA (CHO-HveA cells) and CHO-K1 cells expressing HveC (CHO-HveC cells), CHO-250-2, and CHO-R3 cells were grown in Ham's F-12 medium supplemented with 10% (v/v) FBS and 200 micrograms per milliliter of G418. KOS-hrR3 virus is a mutant KOS virus in which the *E. coli* lacZ gene is positioned in the ribonucleotide reductase large subunit locus (ICP6) under the transcriptional control of the ICP6 promoter. This virus was propagated in African green monkey kidney (Vero) cells expressing the large subunit of HSV type 1 ribonucleotide reductase as described (Golstein and Weller, 1988, J. Virol. 62:196–205). Vero cells were grown in Dulbecco's minimal essential medium supplemented with 5% (v/v) fetal calf serum (FCS), at 37° C.

Construction of Phage Libraries

A library ("the 27-mer library") comprising about $2\times10^8$ recombinant M13 phages was constructed, each phage comprising pIII protein having the amino acid sequence SR $X_{12}$ (S, P, T, or A) A (V, A, D, E, or G) $X_{12}$ SR (wherein standard single-letter amino acid codes are used, "X" being a random amino acid residue) at its N-terminus. Nucleic acids encoding the random peptides regions were constructed by annealing and extending two long degenerate oligonucleotides which were complementary at their 3' end, as described (Sahu et al., 1996, J. Immunol. 157:884–891; Kay et al., 1993, Gene 128:59–65). Six complementary nucleotides of these degenerate oligonucleotides form a SacII restriction site and encode the tripeptide sequence (S/P/T/A) A (V/A/D/E/G), as described (Adey and Kay, 1996, Gene 169:133–134).

Another library ("the 12-mer library") comprising about $10^8$ recombinant M13 phages, was constructed, each phage comprising pIII protein having the amino acid sequence $X_{12}$ at its N-terminus. The library was constructed by annealing and extending two oligonucleotides, one of which was degenerate.

The codon encoding each random amino acid residue (i.e., each X) in both of these libraries had the nucleotide sequence NNK, where N was, randomly, one of A, C, G and T, and K was, randomly, G or T. This codon is capable of encoding each of the 20 naturally-occurring amino acid residues, and some residues are encoded by two (A, G, P, V, T), or three (L, R, S) codons which conform to this sequence.

Biopanning of Phage Libraries

HveA-binding phages were isolated by screening the 27-mer and the 12-mer libraries, as described (Sahu et al., 1996, J. Immunol. 157:884–891; Kay et al., 1993, Gene 128:59–65). Microtiter wells (Nunc, Inc., Naperville, Ill.) were coated overnight at 4° C. or for 2 hours at 22° C. with 500 nanograms of HveA (200t) and were blocked using PBS containing 1% (w/v) BSA for 1 hour at 22° C. After washing, about $6\times10^{11}$ plaque-forming units (PFU) of each library were added to each well and incubated for 1 hour at 22° C. The wells were washed twice with PBS containing 0.05% (v/v) Tween-20. Bound phage particles were eluted using 100 millimolar glycine-HCl, pH 2.3, and the samples were immediately neutralized using 200 millimolar sodium phosphate, pH 7.4. Eluted phage particles were amplified in *E. coli* DH5α F', and the biopanning procedure was repeated twice. The amplified phage mixture obtained after the third round of amplification was plated, and "positive" phage were identified by confirming their ability to bind with HveA (200t) using an ELISA in which bound phages were detected using peroxidase-labeled anti-M13 antibody (Amersham Pharmacia, Piscataway, N.J.). DNA was isolated from "positive" phage stocks and subjected to dideoxy sequencing using the Sanger method as described (Sambrook et al., 1989, Molecular Cloning: A Laboratory Manual, Cold Spring Harbor, N.Y.).

Synthesis and Purification of Peptides

Two synthetic peptides corresponding to the phage-displayed HveA-binding peptides (BP-1 and BP-2) and their analogs BP-1(4, 10 Acm), BP-2 (3, 9 Ala), and scrambled BP-2, were synthesized using an Applied Biosystem peptide synthesizer (Model 431A, Foster City, Calif.) using F-moc amide resin. The side chain protecting groups were: Cys (Trt), Cys (Acm), Arg (Pmc), Ser (tBu), and Tyr(tBu).

BP-1 and BP-1(4, 10 Acm) were cleaved from the resin by incubation for 3 hours at 22° C. with a solvent mixture containing 5% (v/v) phenol, 5% (v/v) thioanisole, 5% (v/v) water, 2.5% (v/v) ethanedithiol, and 82.5% (v/v) trifluoroacetic acid (TFA). The reaction mixture was filtered through a fritted funnel, precipitated with cold ether, dissolved in 50% (v/v) acetonitrile containing 0.1% (v/v) TFA, and lyophilized. Disulfide oxidation of BP-1 was performed by stirring a 0.15 millimolar solution of peptide in 0.1 molar ammonium bicarbonate, pH 8.0, and bubbling with oxygen at 22° C. for 48 hours. Reduced and alkylated BP-1, i.e., BP-1 (4, 10 Acm), was obtained by reducing BP-1 with 10 millimolar dithiothreitol (DTT) and alkylating the peptide using 40 millimolar iodoacetamide.

BP-2 and scrambled BP-2 were cyclized in resin. Relative to cyclization in solution, this method avoids the formation of multimeric material and avoids time-consuming lyophilization and purification steps. The peptides were treated with 1.5 equivalents of thallium(III)trifluoroacetate in dimethylformamide (DMF) for 3 hours at 22° C., which effects a selective deprotection of the two Cys residues and subsequent oxidation of the Cys-thiol to a disulfide. Resin-bound peptides were washed with DMF, methanol, methanol:dichloromethane (60:40) and were under vacuum. Peptides were cleaved from the peptide-resin by treatment with 87.5% (v/v) TFA, 5% (v/v) phenol, 5% (v/v) water, and 2.5% (v/v) triisopropylsilane for 3 hours at 2° C. Peptides were harvested from the reaction mixture by filtration and precipitated in cold ether. After extracting the peptide precipitates three times with cold ether, peptide pellets were dissolved in 50% (v/v) acetonitrile containing 0.1% (v/v) TFA and lyophilized.

Crude peptides were dissolved in 10% (v/v) acetonitrile containing 0.1% (v/v) TFA and purified by reversed-phase high-performance liquid chromatography (RP-HPLC). RP-HPLC was performed using an automated system (Waters Prep-LC 4000™, Milford, Mass.) equipped with a $C_{18}$ column (Vydac™, Western Analytical Products, Murrieta, Calif.). The column was initially developed using buffer A (0.1% (v/v) TFA in water) for 10 minutes, and peptide fractions were eluted using a 25 minute linear gradient of 500 milliliters of 5–90% buffer B (0.1% (v/v) TFA in acetonitrile) at a flow rate of 20 milliliters per minute. The elution profile of the peptide fractions was monitored by UV detection at 230 nanometers and the major peak containing the desired peptide was collected and lyophilized. The purity of final products was assessed by matrix-assisted laser desorption mass spectrometry (MALDI-MS) using a time-of-flight mass spectrometer (MicroMass TofSpec™, Micromass, Inc., Beverly, Mass.).

ELISAs

Several ELISAs were performed to analyze interaction among HveA, the isolated phage peptides, gD, and LT-α. In these assays, microtiter wells were coated for 2 hours at 22° C. with 40 nanograms of HveA(200t), human factor H, trout complement C3, BSA, milk, or ovalbumin. Nonspecific binding in the wells was blocked using PBS containing 1% (w/v) BSA for 1 hour at 22° C. For competition assays, serial dilutions of gD-1 (306t), gD-1 (Δ290–299t), BSA, peptide BP-1, BP-2, or an unrelated cyclic peptide having the amino acid sequence ICVVQDWGHHRCT (SEQ ID NO:3) was added to each well. After 30 minutes of incubation at 22° C., recombinant protein (i.e., gD-1 (306t) at 0.4 microgram per milliliter, gD-1 (Δ290–299t) at 0.1 microgram per milliliter, or LT-α at 20 nanomolar), or phage supernatant was added to the well, and the samples were incubated for 1 hour. The wells were washed twice with PBS containing 0.05% (v/v) Tween-20 and incubated for one hour at 22° C. with at least one of the following: (i) a 1:1000 dilution of a peroxidase-labeled anti-M13 antibody, (ii) a 1:400 dilution of an anti-gD polyclonal antibody (R7), or (iii) an anti-LT-α monoclonal antibody (AG9).

Following incubation with the antibody, the wells were washed twice with PBS containing 0.05% (v/v) Tween-20 and incubated for 30 minutes at 22° C. with a 1:1000 dilution of a peroxidase-conjugated goat anti-rabbit immunoglobulin G (for polyclonal antibody detection) or with goat anti-mouse immunoglobulin G (for monoclonal antibody detection; Bio-Rad Laboratories, Richmond, Calif.). Color was developed by adding 2,2'-azino-di-(3-ethylbenzthiazolinesulfonate) (ABTS, Boehringer-Mannheim, Indianapolis, Ind.) and 0.5% (v/v) hydrogen peroxide. Absorbance was assessed at 405 nanometers. Net gD-1 or LT-α binding was calculated by subtracting the amount of secondary antibody bound with HveA from the amount of ligand bound with HveA.

HSV Entry Assays

CHO-HveA, CHO-HveC, and Vero cells were plated on 96-well dishes and incubated overnight. The cells were chilled at 4° C. for 10, minutes and then the medium was replaced with Ham's F-12 (CHO-HveA and CHO-HveC cells) or with Dulbecco's modified Eagle medium (DMEM) (Vero cells). These media were supplemented with 10% (v/v) bovine fetal serum and 10 millimolar HEPES, containing various concentrations of peptide, which had been previously filtered through a 0.2 micrometer pore size filter (Corning Glass Works, Corning, N.Y.). The plates were rocked at 4° C. for 90 minutes, at which time KOS-hrR3 virus ($5 \times 10^5$ PFU/well) was added. The plates were rocked at 4° C. for 90 additional minutes and then incubated at 37° C. for 5 hours. Cells were lysed using 20% (v/v) Nonidet P-40 and β-galactosidase substrate (o-nitrophenyl-β-D-glucopyranoside) was added to each well. β-galactosidase activity was measured at selected time points using a Specromax 250 enzyme-linked immunosorbent assay (ELISA) reader.

The Results of the experiments presented in this example are now described.

Isolation and Characterization of HveA-binding Phages

To isolate peptide ligands which interact with HveA, two phage-displayed random combinatorial peptide libraries that contained about $2 \times 10^8$ and $10^8$, respectively, unique phage clones expressing random peptides 27 and 12 amino acid residues in length, respectively, were screened. Phage particles expressing HveA-binding peptides were affinity purified by plating on a microtiter plate coated with HveA (200t). After a third round of biopanning, individual phage clones were isolated and tested for binding with HveA.

Figure 1A:
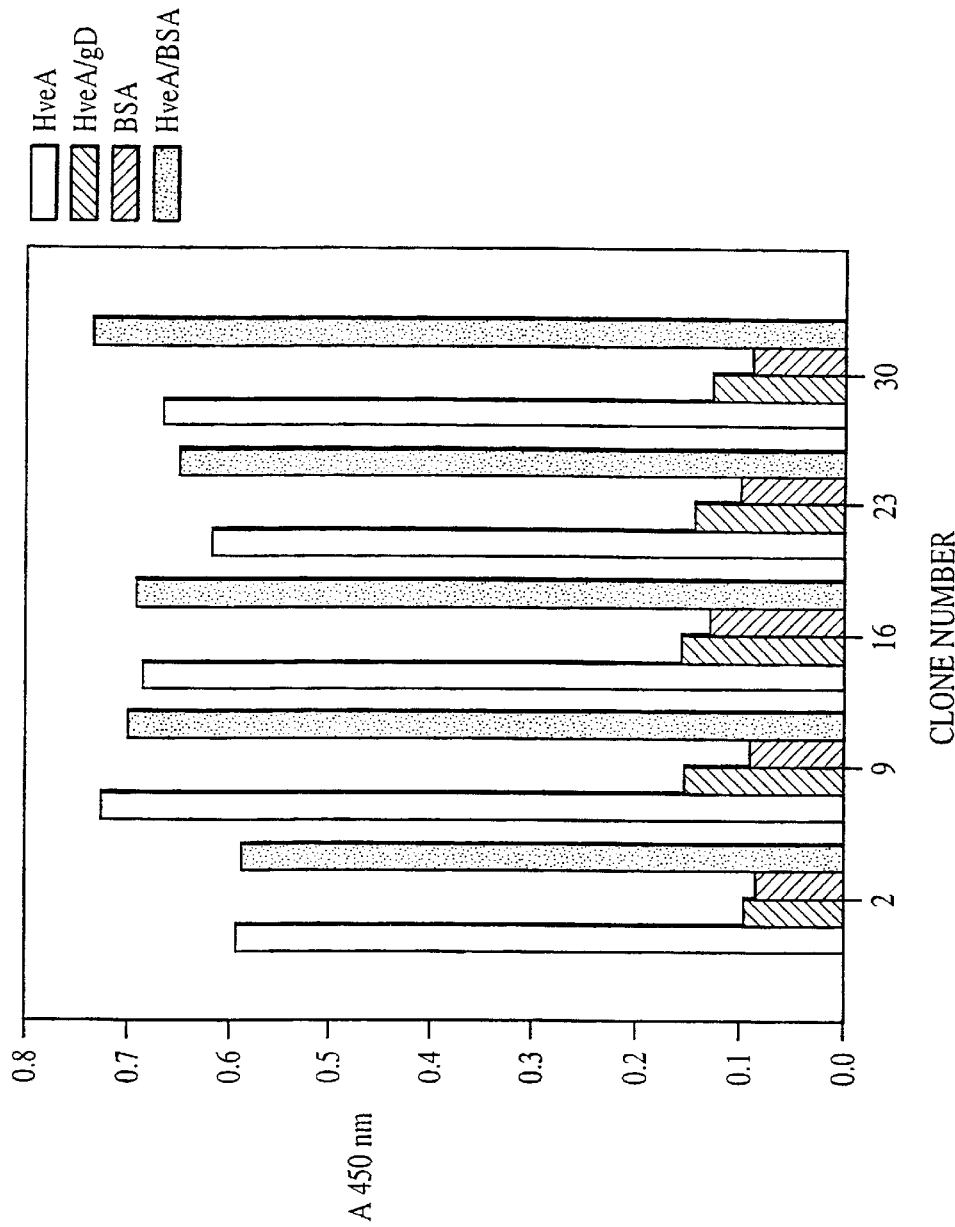
FIG. 1A is a bar graph depicting specific binding with HveA of positive clones isolated from two phage-displayed random peptide phage display libraries.
Figure 1B:
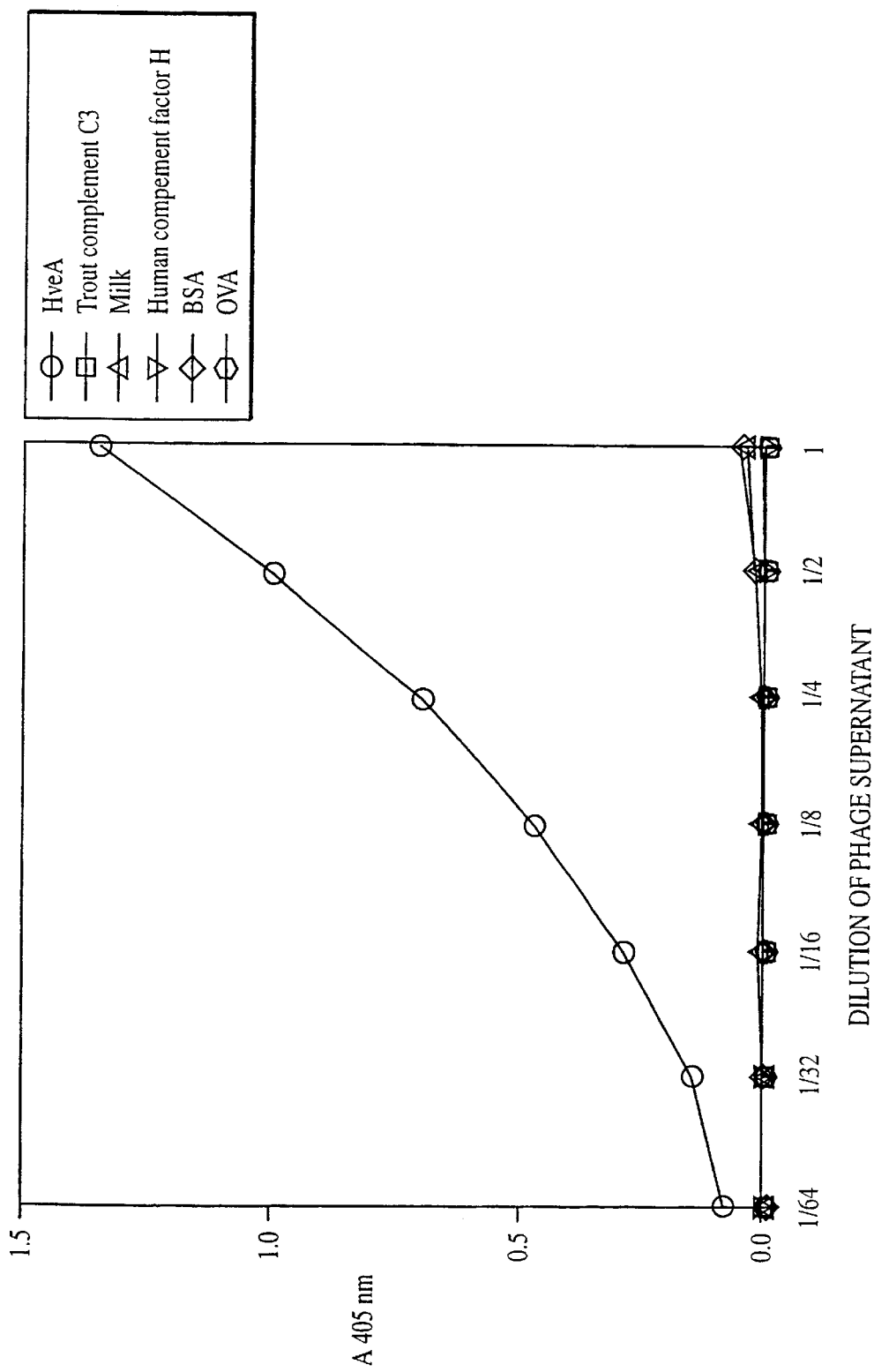
FIG. 1B is a graph depicting specific binding with HveA by a clone isolated from a random peptide phage display library.

To demonstrate that binding of isolated phage clones with HveA was specific for HveA, a competition ELISA was performed in which fluid-phase soluble gD-1 (306t) significantly inhibited phage binding with HveA(200t). The results of these experiments are depicted in FIG. 1A. Furthermore, HveA-binding phages did not bind to trout complement C3, milk, OVA, BSA or human complement factor H in direct ELISA, as indicated by the results depicted in FIG. 1B.

DNA obtained from several positive clones was purified and subjected to dideoxy sequencing. All positive clones from each of the libraries had the same sequence, which indicates that the clones were specific and had been amplified during biopanning.

The deduced amino acid sequences of the clones are indicated in FIG. 2. BP-1 was obtained from the 27-mer library, and BP-2 from the 12-mer library. The amino acid sequence of the BP-1 clones from the 27-mer library does not agree with the intended amino acid sequence of the library {SR $X_{12}$ (S, P, T, or A) A (V, A, D, E, or G) $X_{12}$ SR}. Without wishing to be bound by theory, the inventors believe that the SacII recognition site (i.e. the region of complementarity of the two degenerate oligonucleotides used for the construction) may have been modified during generation of the library. The sequence of the isolated clones in this region is P R, instead of the expected (S, P, T, or A) A (V, A, D, E, or G). Thus, BP-1 is only 26 amino acids in length.

Neither of BP-1 or BP-2 exhibited similarity to any known protein as assessed by searching the GenBank (DNA) and SwissProt (protein) databases using BlastP, BlastN, and BlastX algorithms.

To further characterize the binding properties of the isolated clones, two peptides were synthesized which corresponded to the deduced amino acid sequence of the phage-displayed peptides, namely BP-1 and BP-2. In addition, two peptides analogous to BP-2 were synthesized. The first analogous peptide, designated BP-2 (3, 9 Ala), is a linear form of BP-2 which was generated by substitution of the cysteine residues with alanine residue. BP-2 (3, 9 Ala) was used to determine whether the disulfide bond in BP-2 is important for the structure and activity of the cyclic BP-2 peptide. The second analogous peptide, designated scrambled BP-2, having the scrambled primary sequence of the parental cyclic BP-2, but maintaining the position of the two cysteines, was used to determine if the activity of BP-2 is sequence specific. A linear BP-1 peptide, designated BP-1 (4, 10 Acm), was generated by reduction and alkylation of the 26-mer peptide. The structures of these compounds are depicted in FIG. 2.

Figures 3A, 3B:
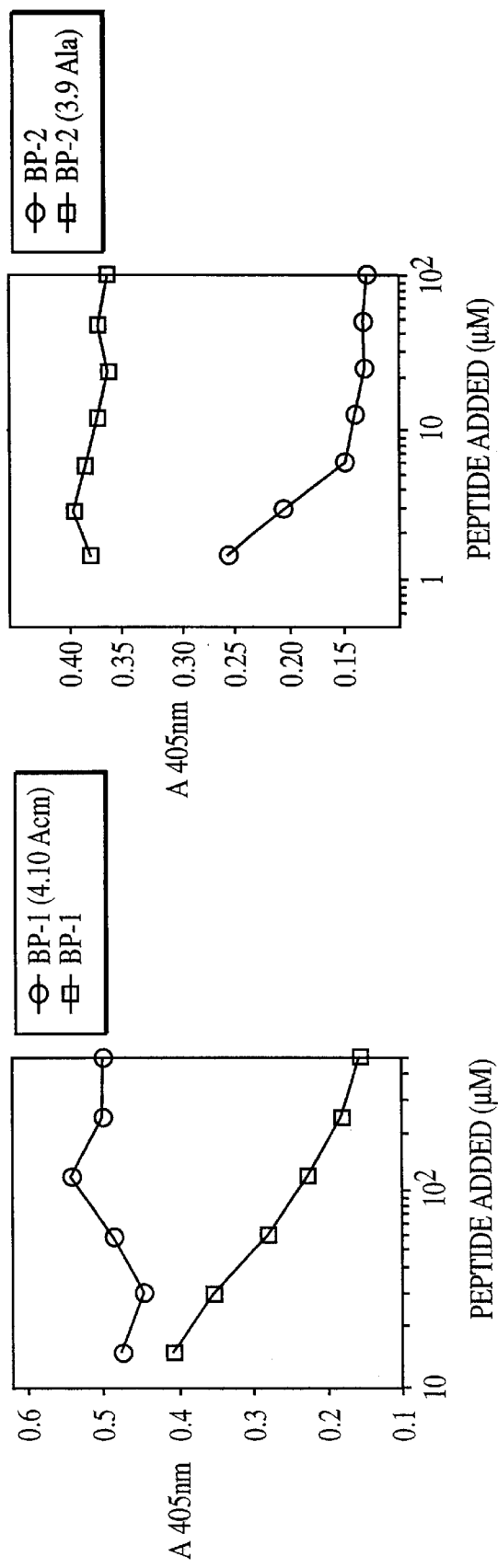
FIG. 3A is a graph depicting inhibition of BP-2 binding with HveA mediated by BP-1 (■) or (BP-1 (4,10 Acm) (●).
FIG. 3B is a graph depicting inhibition of BP-1 binding with HveA mediated by BP-2.

Although the two isolated clones are not similar in sequence, binding of phage displaying BP-1 to HveA was inhibited in an ELISA by peptide BP-2, and vice versa, as indicated by the results depicted in FIGS. 3A and 3B.

Inhibition of gD-1 Binding to HveA

The peptides, BP-1 and BP-2, corresponding to the deduced amino acid sequences of the phage-displayed peptides, were tested in a competition ELISA for the ability to compete with gD-1 for binding with the HveA receptor.

Figures 4A, 4B:
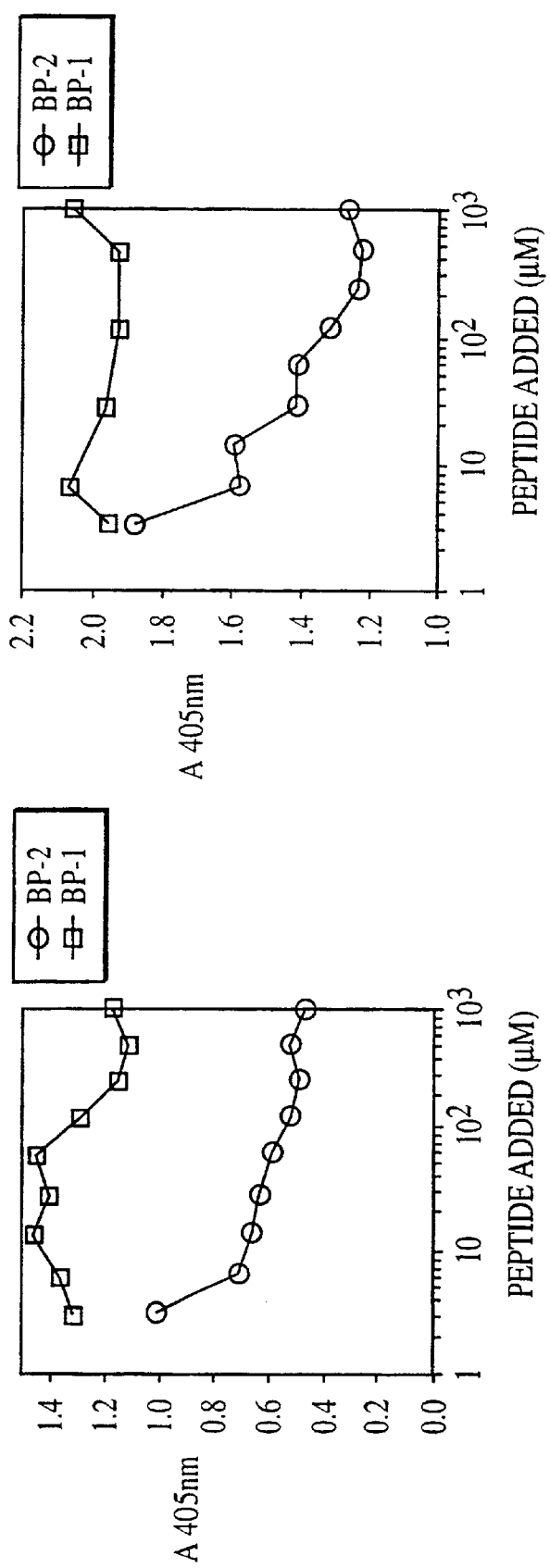
FIG. 4A is a graph depicting inhibition of gD-1 (306t) binding with HveA mediated by BP-2 (●) or BP-1 (■).
FIG. 4B is a graph depicting inhibition of gD-1 (Δ290–299t) binding with HveA mediated by BP-2 (●) or BP-1 (■).

Binding of soluble wild type gD-1, gD-1(306t), with immobilized HveA (200t) was inhibited by BP-2 at a level of 80% and by BP-1 at a level of 20% at a concentration of 0.5 millimolar, as indicated by the data disclosed in FIG. 4A.

Binding of the mutant form of gD-1 (Δ290–299t), which has a 100-fold higher affinity for HveA, was inhibited at a level of 40% by BP-2 as indicated by the data disclosed in FIG. 4B.

Figure 4C:
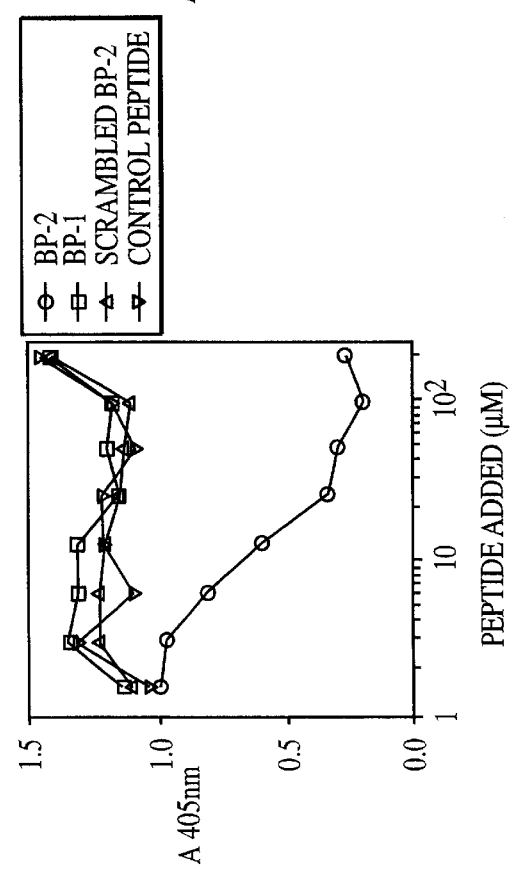
FIG. 4C is a graph depicting inhibition of gD-1 (306t) binding with HveA mediated by BP-2 (●), BP-1 (■), Scrambled BP-2 (▲),or Control peptide (▼).

As indicated by the data disclosed in FIG. 4C, no inhibitory effect upon binding of gD-1 with HveA was observed using BP-1 (4, 10 Acm), BP-2 (3, 9 Ala), scrambled sequence BP-2, or a cyclic control peptide with a completely different sequence (ICVVQDWGHHRCT; SEQ ID NO:3). The effects of BP-2 and BP-1 on binding with gD was specific to these peptides, since neither an unrelated peptide or the peptide analogs (BP-1 (4, 10 Acm), BP-2 (3, 9 Ala). or scrambled sequence BP-2) exhibited an inhibitory effect. Because these negative results included peptides BP-1 (4, 10 Acm) and BP-2 (3, 9 Ala), in which no disulfide bond is present, it appears that disulfide bond formation is important for maintaining the inhibitory activity of both BP-1 and BP-2.

Inhibition of LT-α Binding to HveA

Figure 5:
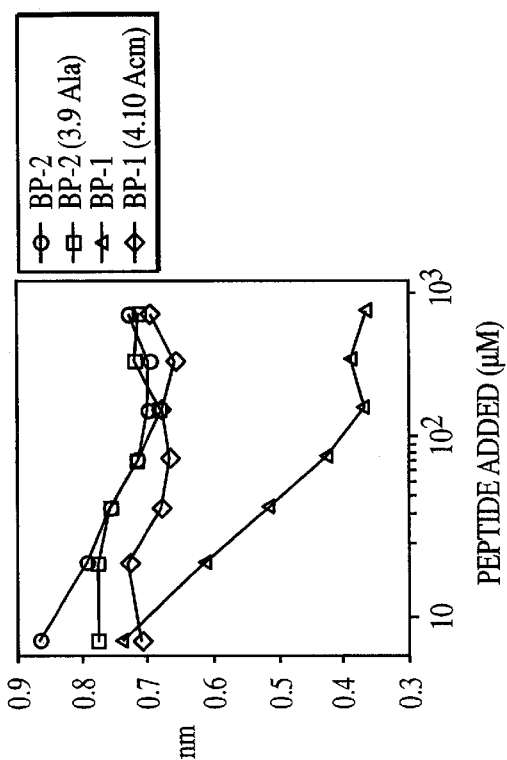
FIG. 5 is a graph depicting inhibition of lymphotoxin α (LT-α) binding with HveA mediated by BP-1 but not by BP-2, BP-2 (3, 9 Ala), or BP-1 (4, 10 Acm).

The effect of synthetic peptides BP-1 and BP-2 on LT-α binding with HveA was analyzed by ELISA. HveA was coated onto the wells of a microtiter plate and incubated with various concentrations peptides along with 20 nanomolar LT-α, and the amount of LT-α bound was detected using a monoclonal antibody. As indicated in FIG. 5, binding of soluble LT-α with HveA was inhibited by BP-1, whereas none of the other peptides exerted an inhibitory effect on this binding. These data demonstrate that cyclization of peptide BP-1 is necessary for binding of BP-1 with HveA. On the other hand, BP-2 did not inhibit LT-α binding with HveA, suggesting that BP-1 and BP-2 bind to different sites on HveA.

Inability of gD to Inhibit LT-α Binding to HveA

Figure 6:
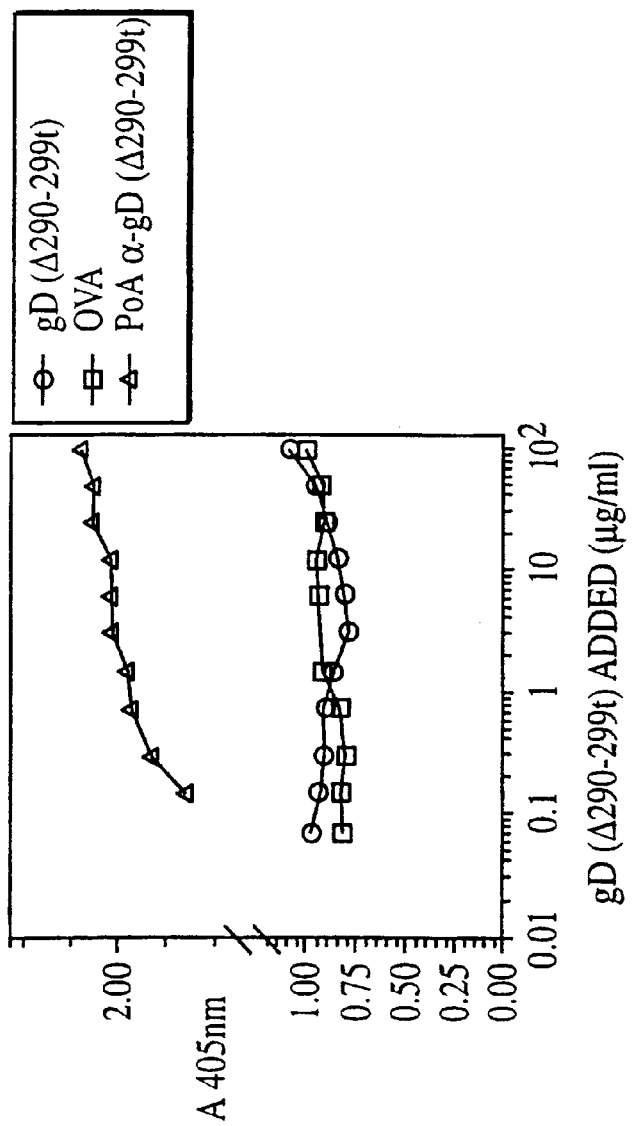
FIG. 6 is a graph depicting lack of competition by gD-1 with binding of LT-α and HveA.

Given that the data disclosed elsewhere herein demonstrated that BP-1 and BP-2 appear to bind different sites on HveA, the ability of gD and LT-α, which are both natural ligands of HveA, to bind HveA in a competitive manner, was determined and the results of these experiments are depicted in FIG. 6. The relative amounts of gD and LT-α bound with HveA were assessed by ELISA. In this assay, HveA was first immobilized on the microtiter plate wells, and then the wells were incubated with a constant amount of LT-α in the presence of various amounts of gD. The amount of LT-α bound to HveA was detected using a monoclonal antibody to LT-α (AG9). To confirm that gD remained bound to HveA during the wash steps, bound gD was detected using a polyclonal anti-gD antibody (R7) in separate wells of the same ELISA microtiter plate. The data presented in FIG. 6 indicate that the same amount of LT-α bound with HveA regardless of the amount of gD added to the wells. Thus, gD had no inhibitory effect on LT-α binding with the receptor, indicating that gD and LT-α do not compete for the same binding sites on HveA.

Inhibition of HSV-1 Entry into Cells by BP-1 and BP-2

Figures 7A, 7B:
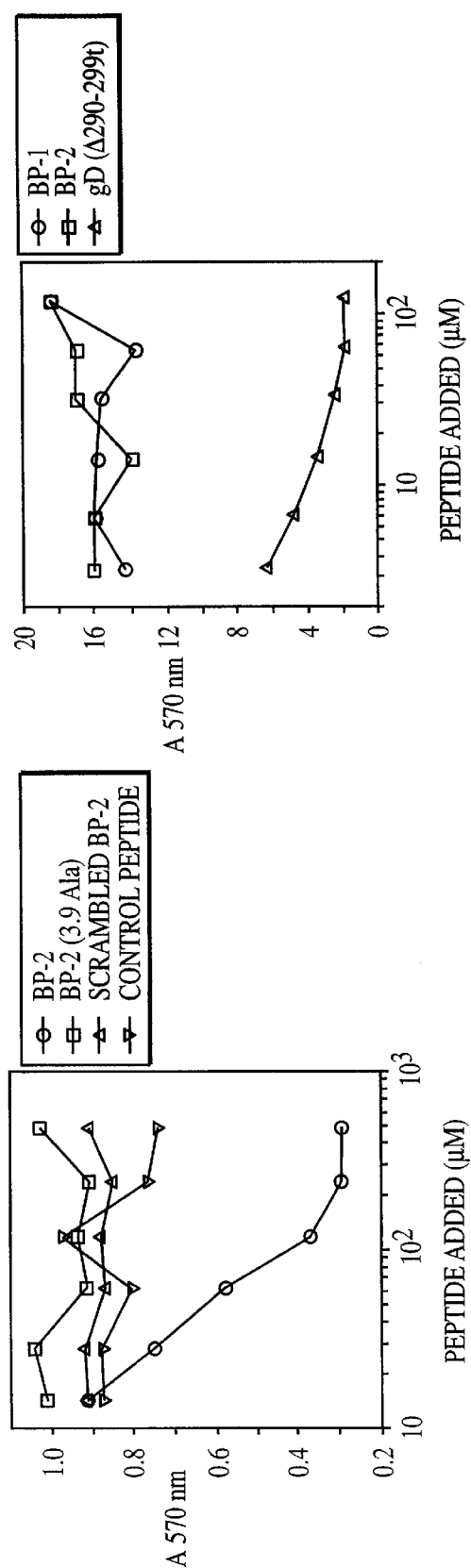
FIG. 7A is a graph depicting the effect of BP-2 and its analogs on HSV-1 entry into CHO-HveA cells. The effects of the following peptides was assessed: BP-2 (●); BP-2 (3, 9 Ala) (■); scrambled BP-2 (▲); and an unrelated (control) peptide (▼).
FIG. 7B is a graph depicting the effect of BP-1, BP-2, and gD (Δ290–299t) on HSV-1 entry into Vero cells. The effects of the following peptides was assessed: BP-1 (●); BP-2 (■); and gD (Δ290–299t) (▲).

Inhibition of gD-1 binding with HveA mediated by BP-2, as indicated in FIGS. 4A–4C, raised the question of whether this peptide has a blocking effect on viral entry into mammalian cells. To test this possibility, the effect of BP-2 and related peptides (i.e., BP-1, BP-2 (3, 9 Ala), scrambled BP-2, control peptide, and gD-1(Δ290–299t)) on HSV-1 entry into CHO cells expressing either HveA (CHO-HveA cells), or HveC (CHO-HveC cells), and into Vero cells was examined. Cell monolayers were incubated with increasing concentrations of peptide at 4° C. for 90 minutes. Following incubation, the cells were infected with the β-galactosidase reporter virus, KOS-hrR3. The results of these experiments are depicted in FIGS. 7A and 7B.

BP-2 blocked entry of HSV-1 into CHO-HveA cells. In contrast, neither BP-1 nor any of the BP-2 analogs blocked virus entry. Neither BP-1 or BP-2 had any effect on HSV entry into Vero or CHO-HveC cells. Thus, although both BP-1 and BP-2 bind with HveA, only BP-2 is able to inhibit gD-1 binding with HveA in such a way as to block HSV-1 entry into CHO-HveA cells. This result is consistent with the data demonstrating that only BP-2 effectively blocked gD binding with HveA.

The marginal effect observed on inhibition of fluid-phase gD binding with HveA mediated by BP-1 contrasts the effect mediated by BP-2, which inhibited not only binding of soluble gD-1(306t) with HveA but also binding with HveA of soluble gD-1(Δ290–299t) (Nicola et al., 1996, J. Virol. 70:3815–3822; Whitbeck et al., 1997, J. Virol. 71:6083–6093; Willis et al., 1998, J. Virol. 72:5937–5947). Furthermore, BP-2 blocked viral entry into CHO-HveA cells, where gD-1(306t) failed to do so. Without wishing to be bound by any particular theory of operation, the inventors believe that BP-2 has a higher affinity for HveA than does wild-type gD-1(306t), and therefore large amounts of gD-1 (306t) are required for inhibition.

The failure of BP-2 to block viral entry into CHO-HveC cells suggests that BP-2 binds specifically with HveA. Because BP-2 also fails to block HSV entry into Vero cells, entry mediators other than or in addition to HveA are expressed by these cells. Alternatively, it is possible that the site in HveA with which the peptides bind is not conserved among primate homologs of HveA.

The differential inhibitory effects of the two peptides with respect to LT-α and gD binding with HveA suggest that BP-1 and BP-2 bind with different sites on HveA. Because binding of BP-1 with HveA is inhibited by BP-2, and vice versa, it may be that either the peptides bind to overlapping sites on HveA, or that binding of one peptide with HveA induces a conformational change in HveA that influences the binding of the other peptide. BP-1 and BP-2 partially have a common binding site on HveA and compete for binding with that site. Accordingly, although LT-α binding with HveA was inhibited only by BP-1, the HveA site to which gD binds can include structural elements involved in the binding of both peptides. In this way, both peptides could affect the interaction between gD and HveA. However, BP-1 only partially inhibits binding of gD with HveA. Thus, it appears that the gD-binding site of HveA is nearer the BP-2 site than the BP-1 site.

The inhibitory effect of BP-2 with respect to gD binding with HveA, which led to inhibition of HSV entry into CHO-HveA cells, indicates that BP-2 has a high affinity for the receptor. In addition, BP-2 can compete with gD for more than one binding site on HveA. This is consistent with a recent study in which monoclonal antibodies recognizing two different regions on gD, namely regions Ib (amino acid residues 222 to 252) and VII (amino acid residues 11 to 19), were found to block HSV binding to HveA (Nicola et al., 1998, J. Virol. 72:3595–3601). If the peptides bound with overlapping sites on HveA, then gD and LT-α would bind to adjacent sites on the receptor.

A second interpretation of the data described herein is that binding of the peptides to the receptor causes conformational changes in HveA. Thus, BP-1 binding with HveA causes a conformational change in the receptor that interferes with BP-2, LT-α, and gD binding with HveA. On the other hand, BP-2 binding with HveA can alter BP-1 and gD binding sites on HveA.

The data disclosed herein demonstrate that one site on HveA, where BP-2 binds, which when it is occupied prevents viral uptake but not the binding of a cellular ligand, LT-α. Screening chemical compound libraries for those that displace BP-2 but not BP-1 can be useful to identify useful agents to prevent HSV infection.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A peptide selected from the group consisting of SEQ ID NO:4 and SEQ ID NO:5.

2. The peptide of claim 1, wherein the peptide inhibits binding of herpes simplex virus (HSV) gD with HveA, herpesvirus entry mediator protein.

3. The peptide of claim 1, wherein the peptide is SEQ ID NO:4.

4. The peptide of claim 1, wherein the peptide is SEQ ID NO:5.

5. The peptide of claim 1, wherein the peptide inhibits entry of an HSV into a cell.

6. The peptide of claim 5, wherein the HSV is selected from the group consisting of HSV-1 and HSV-2.

7. A method of comprising contacting HveA, herpesvirus entry mediator protein, with a peptide selected from the group consisting of SEQ ID NO:4 and SEQ ID NO:5 thereby inhibiting the ability of HveA, herpesvirus entry mediator protein, to bind with HSV gD in vitro.

* * * * *

SEQUENCE LISTING

```
<160> NUMBER OF SEQ ID NOS: 6

<210> SEQ ID NO 1
<211> LENGTH: 26
<212> TYPE: PRT
<213> ORGANISM: Artificial Sequence
<220> FEATURE:
<223> OTHER INFORMATION: Peptide corresponds to BP-1(4,10 Acm)

<400> SEQUENCE: 1

Ser Ile Ser Cys Ser Arg Gly Leu Val Cys Leu Leu Pro Arg Leu Thr
1               5                   10                  15

Asn Glu Ser Gly Asn Asp Arg Phe Asp Ser
            20                  25

<210> SEQ ID NO 2
<211> LENGTH: 12
<212> TYPE: PRT
<213> ORGANISM: Artificial Sequence
<220> FEATURE:
<223> OTHER INFORMATION: Peptide corresponds to BP-2 (3,9 Ala)

<400> SEQUENCE: 2

Gly Ser Ala Asp Gly Phe Arg Val Ala Tyr Met His
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Peptide corresponds to Control Peptide

<400> SEQUENCE: 3

Ile Cys Val Val Gln Asp Trp Gly His His Arg Cys Thr
1               5                   10

<210> SEQ ID NO 4
```

-continued

<211> LENGTH: 26
<212> TYPE: PRT
<213> ORGANISM: Artificial Sequence
<220> FEATURE:
<223> OTHER INFORMATION: Peptide corresponds to BP-1

<400> SEQUENCE: 4

Ser Ile Ser Cys Ser Arg Gly Leu Val Cys Leu Leu Pro Arg Leu Thr
1 5 10 15

Asn Glu Ser Gly Asn Asp Arg Phe Asp Ser
20 25

<210> SEQ ID NO 5
<211> LENGTH: 12
<212> TYPE: PRT
<213> ORGANISM: Artificial Sequence
<220> FEATURE:
<223> OTHER INFORMATION: Peptide corresponds to BP-2

<400> SEQUENCE: 5

Gly Ser Cys Asp Gly Phe Arg Val Cys Tyr Met His
1 5 10

<210> SEQ ID NO 6
<211> LENGTH: 12
<212> TYPE: PRT
<213> ORGANISM: Artificial Sequence
<220> FEATURE:
<223> OTHER INFORMATION: Peptide corresponds to scrambled BP-2

<400> SEQUENCE: 6

Tyr Met Cys Arg Phe Val Asp Gly Cys His Gly Ser
1 5 10